United States Patent
Gee (10) Patent No.: US 11,186,530 B2
(45) Date of Patent: Nov. 30, 2021

(54) BRANCHED $C_{18}$ OLEFINS PRODUCED BY METATHESIS OF BRANCHED $C_{10}$ OLEFINS

(71) Applicant: Chevron Phillips Chemical Company LP, The Woodlands, TX (US)

(72) Inventor: Jeffrey C. Gee, Kingwood, TX (US)

(73) Assignee: Chevron Phillips Chemical Company, LP, The Woodlands, TX (US)

(*) Notice: Subject to any disclaimer, the term of this patent is extended or adjusted under 35 U.S.C. 154(b) by 105 days.

(21) Appl. No.: 16/850,375

(22) Filed: Apr. 16, 2020

(65) Prior Publication Data

US 2021/0323896 A1    Oct. 21, 2021

(51) Int. Cl.
*C07C 6/04*     (2006.01)
*C07C 11/02*    (2006.01)

(52) U.S. Cl.
CPC .............. *C07C 6/04* (2013.01); *C07C 11/02* (2013.01)

(58) Field of Classification Search
None
See application file for complete search history.

(56) References Cited

U.S. PATENT DOCUMENTS

| 8,765,984 B2 | 7/2014 | Upshaw |
| 2003/0135080 A1 | 7/2003 | Botha et al. |
| 2003/0224945 A1 | 12/2003 | Twu et al. |
| 2018/0016204 A1 | 1/2018 | Coffin et al. |

FOREIGN PATENT DOCUMENTS

WO    2017011127 A1    1/2017

OTHER PUBLICATIONS

Deckers, Patrick J. W., et al., "Catalytic Trimerization of Ethene with Highly Active Cyclopentadienyl-Arene Titanium Catalysts," Organometallics, 2002, vol. 21, pp. 5122-5135, American Chemical Society.
Do, Loi H., et al., "Mechanistic Studies of Ethylene and α-Olefin Co-Oligomerization Catalyzed by Chromium-PNP Complexes," Organometallics, 2012, vol. 31, pp. 5143-5149, American Chemical Society.
Zhou, Yong, et al., "Structural Analysis of Isomers in Commercial Alpha-Olefins with 13C NMR Spectroscopy," Petroleum Processing and Petrochemicals, 2004, vol. 36, No. 5, 15 pages.
Zilbershtein, Timur M., et al., "Decene Formation in Ethylene Trimerization Reaction Catalyzed by Cr-Pyrrole System," Applied Cat A: Gen, 2014, vol. 475, pp. 371-378, Elsevier B.V.
McNaught, Alan D., et al., "Compendium of Chemical Terminology," IUPAC Recommendations, Second edition, 1997, 5 pages, Wiley-Blackwell.

*Primary Examiner* — Ali Z Fadhel
(74) *Attorney, Agent, or Firm* — Conley Rose, P.C.

(57) ABSTRACT

Disclosed herein are compositions containing branched $C_{18}$ disubstituted internal olefins and processes for making the compositions by metathesis reaction of a $C_{10}$ olefin composition.

24 Claims, 1 Drawing Sheet

BRANCHED $C_{18}$ OLEFINS PRODUCED BY METATHESIS OF BRANCHED $C_{10}$ OLEFINS

TECHNICAL FIELD

The present disclosure generally relates to metathesis of branched $C_{10}$ olefins and the branched $C_{18}$ disubstituted internal olefins produced therefrom.

BACKGROUND

Olefin oligomerization reactions produce olefin oligomers using various catalyst systems that can be used to direct reactions to particular oligomer products. For example, aluminum, nickel, zirconium, and iron based catalyst systems can be used for the synthesis of oligomer products containing $C_4$ to $C_{30}$-alpha olefins from ethylene. Chromium based catalyst systems can be used for the selective synthesis of oligomer products containing 1-hexene and/or 1-octene from ethylene. Many applications exist for these oligomer products, including employment as intermediates in the manufacture of detergents, as more environmentally friendly replacements where refined oils might otherwise be used, as monomers or comonomers in the production of polyolefins (e.g., polyethylene), and as intermediates for many other types of products. However, the olefin oligomerization reactions can produce by-products which can be removed from the desired oligomerization product. The oligomerization by-products can have value as commodities, can have value as intermediate chemicals for the synthesis of other higher value products, or can have no value. There is a desire to increase the value of oligomerization by-products.

SUMMARY

Disclosed herein is a composition containing branched $C_{18}$ disubstituted internal olefins. The branched $C_{18}$ disubstituted internal olefins can include 5,12-dimethyl-8-hexadecene, 5-ethyl-11-methyl-7-pentadecene, 5-n-propyl-10-methyl-6-tetradecene, or any combination thereof. The branched $C_{18}$ disubstituted internal olefins can also include 5,10-diethyl-7-tetradecene, 5-n-propyl-9-ethyl-6-tridecene, 5,8-di-n-propyl-6-dodecene, 5-methyl-8-heptadecene, 5-ethyl-7-hexadecene, 5-n-propyl-6-pentadecene, 9-octadecene, or any combination thereof. The branched $C_{18}$ disubstituted internal olefins can also include 5-methyl-8-heptadecene, 5-ethyl-7-hexadecene, 5-n-propyl-6-pentadecene or any combination thereof.

Also disclosed herein is a process for producing the composition containing branched $C_{18}$ disubstituted internal olefins, the process including 1) contacting i) a $C_{10}$ olefin composition comprising branched $C_{10}$ olefins and ii) a metathesis catalyst system; and 2) forming a liquid metathesis product containing the composition containing branched $C_{18}$ disubstituted internal olefins. The branched $C_{10}$ olefins can include $C_{10}$ olefins comprising 3-propyl-1-heptene, 4-ethyl-1-octene, methyl-1-nonene, or any combination thereof and the branched $C_{18}$ disubstituted internal olefins can include 5,12-dimethyl-8-hexadecene, 5-ethyl-11-methyl-7-pentadecene, 5-n-propyl-10-methyl-6-tetradecene, or any combination thereof.

BRIEF DESCRIPTION OF THE DRAWINGS

The following figure forms part of the present specification and is included to further demonstrate certain aspects of the present inventions. The inventions may be better understood by reference to the figure in combination with the detailed description of specific aspects presented herein.

The FIGURE provides the $C_{18}$ portion of a GC/FID chromatogram of the metathesis product of an example $C_{10}$ olefin composition comprising branched $C_{10}$ olefins.

DETAILED DESCRIPTION

Figure 1:
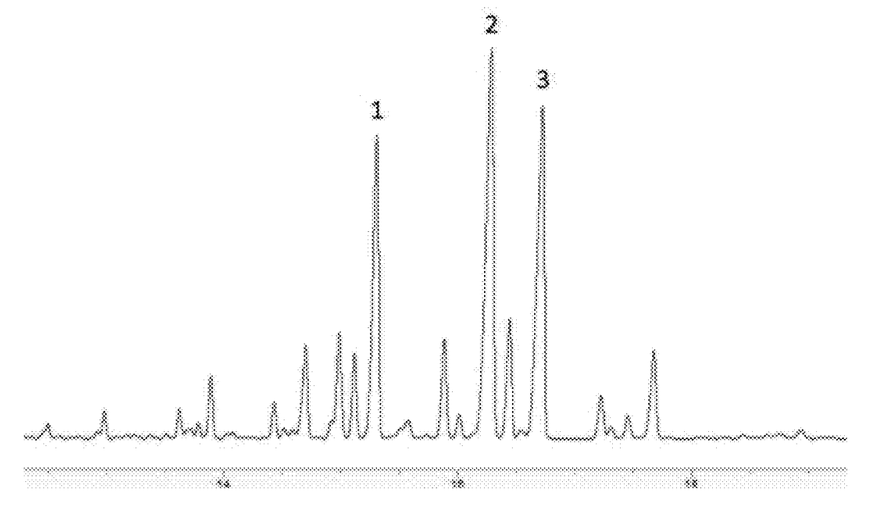

Illustrative aspects of the subject matter claimed herein will now be disclosed. In the interest of clarity, not all features of an actual implementation are described in this specification. It can be appreciated that in the development of any such actual aspect, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure.

In the description herein, various ranges and/or numerical limitations can be expressly stated below. It should be recognized that unless stated otherwise, it is intended that endpoints are to be interchangeable. Further, any ranges include iterative ranges of like magnitude falling within the expressly stated ranges or limitations.

Furthermore, various modifications can be made within the scope of the invention as herein intended, and aspects of the invention can include combinations of features other than those expressly claimed. In particular, flow arrangements other than those expressly described herein are within the scope of the invention.

Unless otherwise specified, the terms "contact" and "combine," and their derivatives, can refer to any addition sequence, order, or concentration for contacting or combining two or more components of the disclosed embodiments. Combining or contacting of metathesis components can occur in one or more reaction zones under suitable contact conditions such as temperature, pressure, contact time, flow rates, etc.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reaction zone" refers to any portion of equipment in which a desired reaction occurs, including but not limited to, a reactor, associated piping, associated pumps, and any other associated equipment. It should be noted that in some cases a "reactor" can also be a "reaction zone." The terms "reactor" and "reaction zone" can be qualified to refer to more specific "reactors" and "reaction zone" by use of additional qualifying terms. For example, the use of the term use of the term "metathesis reactor" and "metathesis reaction zone" indicates that the desired reaction within the reactor and/or reaction zone is a metathesis reaction.

Within this specification, term "reaction zone" refers to the portion of a process, the associated equipment and associated process lines where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction system). For example, in terms of a metathesis process, the reaction zone begins at the point where sufficient feedstock and active catalyst system is present under the sufficient reaction conditions to maintain metathesis product production at the desired rate and the reaction zone ends at a point where either the catalyst system is deactivated, sufficient feedstock is not present to sustain metathesis product production, or other reaction conditions are not sufficient to maintain the metathesis product production or the desired metathesis product production rate. Within this specification the "reaction zone" can comprise one or more reactor zone, one or more reactors, and associated equipment where all the necessary reaction components and reaction conditions are present such that the reaction can occur at a desired rate. The use of the term "metathesis reaction zone" indicates that the desired reaction within the reaction zone is a metathesis reaction.

Unless otherwise indicated, the definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition can be applied. To the extent that any definition or usage provided by any document incorporated herein by reference conflicts with the definition or usage provided herein, the definition or usage provided herein controls.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to hexene includes 1-hexene, 2-hexene, 3-hexene, and any other hydrocarbon having 6 carbon atoms (linear, branched or cyclic) and a single carbon carbon double bond. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc. . . . such multiple bonds can be identified by use of the term "mono," "di," "tri," etc. . . . within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "reaction zone effluent," and it derivatives (e.g., metathesis reaction zone effluent) generally refers to all the material which exits the reaction zone through a reaction zone outlet/discharge which discharges a reaction mixture and can include reaction zone feed(s) (e.g., olefin, catalyst system or catalyst system components, and/or solvent), and/or reaction product (e.g., metathesis product and metathesis by-product). The term "reaction zone effluent" and its derivatives can be qualified to refer to certain portions by use of additional qualifying terms. For example, while reaction zone effluent refers to all material which exits the reaction system through the reaction system outlet/discharge, a reaction zone metathesis product effluent refers to only the metathesis product within the reaction zone effluent.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" any recited maximum value for the feature disclosed herein.

Within this disclosure the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. References to compounds or groups having substitution at positions in addition to the indicated position can be referenced using comprising or some other alternative language. For example, a reference to a phenyl group comprising a substituent at the 4 position refers to a phenyl group having a non-hydrogen substituent group at the 4 position and hydrogen or any non-hydrogen group at the 2, 3, 5, and 6 positions.

Processes and/or, methods described herein can utilize steps, features, and compounds which are independently described herein. The process and/or methods described herein may or may not utilize step identifiers (e.g., 1), 2), etc., a), b), etc., i), ii), etc., or first, second etc., among others), features (e.g., 1), 2), etc., a), b), etc., i), ii), etc., or first, second etc., among others), and/or compound and/or composition identifiers (e.g., 1), 2), etc., a), b), etc., i), ii), etc., or first, second etc., among others). However, it should be noted that processes and/or methods described herein can have multiple steps, features (e.g. reagent ratios, formation conditions, among other considerations), and/or multiple compounds and/or composition using no descriptor or sometimes having the same general identifier. Consequently, it should be noted that the processes and/or methods described herein can be modified to use an appropriate step or feature identifier (e.g., 1), 2), etc., a), b), etc., i), ii), etc., or first, second etc., among others), feature identifier features (e.g., 1), 2), etc., a), b), etc., i), ii), etc., or first, second etc., among others), and/or compound identifier (e.g., first, second, etc.) regardless of step, feature, and/or compound identifier utilized in the a particular statement, aspect, and/or embodiment described herein and that step or feature identifiers can be added and/or modified to indicate individual different steps/features/compounds utilized within the process and/or methods without detracting from the general disclosure.

Terms that indicate the state of matter, such as gas, liquid, solid, and their equivalents, refer to the state of matter at normal temperature and normal pressure; i.e., a temperature of 20° C. (293.15 K, 68° F.) and an absolute pressure of 1 atm (14.696 psi, 101.325 kPa). As used herein, the term "normal conditions" refer to condition of normal temperature (i.e., 20° C., 293.15 K, 68° F.) and normal pressure (i.e., 1 atm, 14.6% psi, 101.325 kPa).

Disclosed herein are compositions having branched $C_{18}$ disubstituted internal olefins and the processes for producing the compositions. Generally, the processes for producing the composition comprising branched $C_{18}$ disubstituted internal olefins can comprise 1) contacting i) a $C_{10}$ olefin composition and ii) a metathesis catalyst system; and 2) forming a metathesis product. In an aspect, the metathesis product can comprise branched $C_{18}$ disubstituted internal olefins. The branched $C_{18}$ disubstituted internal olefins can be used in various applications, such as a feedstock for making alkenyl succinic anhydride (e.g., via reaction with maleic anhydride). The alkenyl succinic anhydride, and/or their derivatives, produced from the $C_{18}$ disubstituted internal olefins can be used as a paper sizing agent or as a lube oil additive, among other uses.

The $C_{10}$ olefin composition, the metathesis catalyst system, the metathesis product, the branched $C_{18}$ disubstituted internal olefins, process steps, and metathesis process conditions for forming the metathesis product are independently described herein and these independent descriptions can be utilized without limitation and in any combination to further describe the processes for producing the metathesis product (e.g., the branched $C_{18}$ disubstituted internal olefins) described herein.

In an aspect, the $C_{10}$ olefin composition which can be utilized in the processes described herein can comprise branched $C_{10}$ olefins; or alternatively, branched $C_{10}$ alpha olefins. In other aspects, and in addition to the branched $C_{10}$ olefins (or branched $C_{10}$ alpha olefins), the $C_{10}$ olefin composition can further comprise linear $C_{10}$ olefins (i.e., a mixture comprising branched $C_{10}$ olefins (or branched $C_{10}$ alpha olefins) and linear $C_{10}$ olefins). In an aspect, the linear $C_{10}$ olefins can be linear alpha olefins. The identity of the branched $C_{10}$ olefins (or branched $C_{10}$ alpha olefins), the amount(s) of each branched $C_{10}$ olefins (or branched $C_{10}$ alpha olefins), the identity of linear $C_{10}$ olefins, the amounts of each linear $C_{10}$ olefin which can be present in the $C_{10}$ olefin composition are independently described herein and these independent descriptions can be utilized in any combination to further describe the $C_{10}$ olefins present in the $C_{10}$ olefin composition utilized for the processes described herein.

In an aspect, the $C_{10}$ olefin composition which can be utilized in the processes disclosed herein can comprise at least 50 mole %, 60 mole %, 65 mole %, 70 mole %, 75 mole %, 80 mole %, 85 mole %, 90 mole %, or 95 mole % branched $C_{10}$ olefins (or branched $C_{10}$ alpha olefins); alternatively or additionally, less than or equal to 99.5 mole %, 99 mole %, 98 mole %, 97 mole %, 95 mole %, 92 mole %, or 90 mole % branched $C_{10}$ olefins (or branched $C_{10}$ alpha olefins). Generally, the $C_{10}$ olefin composition can comprise branched $C_{10}$ olefins (or branched $C_{10}$ alpha olefins) ranging from any minimum branched $C_{10}$ olefins (or branched $C_{10}$ alpha olefins) content disclosed herein to any maximum branched $C_{10}$ olefins (or branched $C_{10}$ alpha olefins) content disclosed herein. For example, in some aspects, the $C_{10}$ olefin composition can comprise from 50 mole % to 99.5 mole %, from 65 mole % to 99 mole %, from 75 mole % to 99 mole %, from 85 mole % to 97 mole %, from 80 mole % to 95 mole %, from 70 mole % to 95 mole %, or from 75 mole % to 90 mole % branched $C_{10}$ olefins (or branched $C_{10}$ alpha olefins). Other ranges for the branched $C_{10}$ olefins (or branched $C_{10}$ alpha olefins) within the $C_{10}$ olefin composition are readily apparent to those skilled in the art with the aid of this disclosure.

In an aspect, the branched $C_{10}$ olefins (or branched $C_{10}$ alpha olefins) of the $C_{10}$ olefin composition can comprise, or can consist essentially of, 3-propyl-1-heptene, 4-ethyl-1-octene, 5-methyl-1-nonene, or any combination thereof; alternatively, 3-propyl-1-heptene, 4-ethyl-1-octene, and 5-methyl-1-nonene; or alternatively, 3-propyl-1-heptene, 4-ethyl-1-octene, 5-methyl-1-nonene, and 2-butyl-1-hexene. In an aspect, the branched $C_{10}$ olefins (or branched $C_{10}$ alpha olefins) of the $C_{10}$ olefin composition can comprise i) at least 8 mole %, at least 9 mole %, at least 10 mole %, at least 11 mole %, at least 12 mole %, or at least 13 mole % 3-propyl-1-heptene, ii) at least 6 mole %, at least 7 mole %, at least 8 mole %, at least 9 mole %, at least 10 mole %, or at least 11 mole % 4-ethyl-1-octene, and/or iii) at least 20 mole %, at least 22 mole %, at least 24 mole %, at least 26 mole %, at least 28 mole %, or at least 30 mole % 5-methyl-1-nonene; alternatively, i) at least 8 mole %, at least 9 mole %, at least 10 mole %, at least 11 mole %, at least 12 mole %, or at least 13 mole % 3-propyl-1-heptene, ii) at least 6 mole %, at least 7 mole %, at least 8 mole %, at least 9 mole %, at least 10 mole %, or at least 11 mole % 4-ethyl-1-octene, iii) at least 20 mole %, at least 22 mole %, at least 24 mole %, at least 26 mole %, at least 28 mole %, or at least 30 mole % 5-methyl-1-nonene, and/or iv) at least 3 mole %, at least 4 mole %, at least 5 mole %, at least 6 mole %, at least 7 mole %, or at least 8 mole % 2-butyl-1-hexene. In another aspect, the branched $C_{10}$ olefins (or branched $C_{10}$ alpha olefins) of the $C_{10}$ olefin composition can comprise i) from 8 mole % to 35 mole %, from 10 mole % to 35 mole %, from 11 mole % to 30 mole %, from 12 mole % to 28 mole %, from 13 mole % to 26 mole %, or from 14 mole % to 24 mole % 3-propyl-1-heptene, ii) from 6 mole % to 30 mole %, from 7 mole % to 30 mole %, from 8 mole % to 25 mole %, from 9 mole % to 23 mole %, from 10 mole % to 22 mole %, or from 11 mole % to 21 mole % 4-ethyl-1-octene, and/or iii) from 20 mole % to 65 mole %, from 24 mole % to 65 mole %, from 26 mole % to 60 mole %, from 28 mole % to 55 mole %, from 30 mole % to 50 mole %, or from 32 mole % to 48 mole % 5-methyl-1-nonene; alternatively, i) from 8 mole % to 35 mole %, from 10 mole % to 35 mole %, from 11 mole % to 30 mole %, from 12 mole % to 28 mole %, from 13 mole % to 26 mole %, or from 14 mole % to 24 mole % 3-propyl-1-heptene, ii) from 7 mole % to 30 mole %, from 7 mole % to 30 mole %, from 8 mole % to 25 mole %, from 9 mole % to 23 mole %, from 10 mole % to 22 mole %, or from 11 mole % to 21 mole % 4-ethyl-1-octene, iii) from 24 mole % to 65 mole %, from 24 mole % to 65 mole %, from 26 mole % to 60 mole %, from 28 mole % to 55 mole %, from 30 mole % to 50 mole %, or from 32 mole % to 48 mole % 5-methyl-1-nonene, and/or iv) from 3 mole % to 25 mole %, from 4 mole % to 22 mole %, from 5 mole % to 20 mole %, from 6 mole % to 18 mole %, or from 7 mole % to 16 mole % 2-butyl-1-hexene.

In an aspect, the $C_{10}$ olefin composition which can be utilized in the processes disclosed herein can comprise a maximum of 50 mole %, 40 mole %, 30 mole %, 25 mole %, 20 mole %, 15 mole % or 10 mole % linear $C_{10}$ olefins (or linear $C_{10}$ alpha olefins); alternatively or additionally, the $C_{10}$ olefin composition can comprise a minimum of 0 mole %, 0.5 mole %, 1 mole %, 1.5 mole %, 2 mole %, or 2.5 mole % linear $C_{10}$ olefins (or linear $C_{10}$ alpha olefins). Generally, the $C_{10}$ olefin composition can comprise linear $C_{10}$ olefins (or linear $C_{10}$ alpha olefins) ranging from any minimum linear $C_{10}$ olefin (or linear $C_{10}$ alpha olefins) content disclosed herein to any maximum linear $C_{10}$ olefin (or linear $C_{10}$ alpha olefins) content disclosed herein. For example, in some non-limiting aspects, the $C_{10}$ olefin composition can comprise from 0 mole % to 50 mole %, from 0.5 mole % to 40 mole %, from 1 mole % to 30 mole %, from 1.5 mole % to 25 mole %, from 2 mole % to 25 mole %, or from 2.5 mole % to 20 mole % linear $C_{10}$ olefins (or linear $C_{10}$ alpha olefins). Other ranges for the linear $C_{10}$ olefins (or linear $C_{10}$ alpha olefins) within the $C_{10}$ olefin composition are readily apparent to those skilled in the art with the aid of this disclosure.

In an aspect, the linear $C_{10}$ olefins (or linear $C_{10}$ alpha olefins) present in the $C_{10}$ olefin composition can comprise (or consist essentially of, or consist of) of 1-decene; alternatively, 4- and/or 5-decene; or alternatively, 1-decene, and 4- and/or 5-decene. In some aspects, the $C_{10}$ olefin composition can comprise a maximum of 40 mole %, 30 mole %, 25 mole %, 20 mole %, 15 mole % or 10 mole % 1-decene; alternatively, or additionally, the $C_{10}$ olefin composition can comprise a minimum of 0 mole %, 0.5 mole %, 1 mole %, 1.5 mole %, 2 mole %, or 2.5 mole % 1-decene. Generally, the $C_{10}$ olefin composition can comprise 1-decene ranging from any minimum 1-decene content disclosed herein to any maximum 1-decene content disclosed herein. For example, in some non-limiting aspects, the $C_{10}$ olefin composition can comprise from 0 mole % to 40 mole %, 0.5 mole % to 30 mole %, 1 mole % to 25 mole %, 1 mole % to 20 mole %, 1 mole % to 15 mole %, 1.5 mole % to 15 mole %, or 1.5 mole to 10 mole % 1-decene. In other aspects, the $C_{10}$ olefin composition can comprise a maximum of 25 mole %, 22.5 mole %, 20 mole %, 19 mole %, or 18 mole % 4- and/or 5-decene; alternatively or additionally, $C_{10}$ olefin composition can comprise a minimum of 0 mole %, 1 mole %, 2 mole %, 3 mole %, 4 mole %, or 5 mole % 4- and/or 5-decene. For example, in some non-limiting aspects, the $C_{10}$ olefin composition can comprise from 0 mole % to 25 mole %, 1 mole % to 20 mole %, 2 mole % to 19 mole %, 3 mole % to 18 mole %, 4 mole % to 17 mole %, 4 mole % to 18 mole %, or 5 mole % to 18 mole % 4- and/or 5-decene. Other ranges for 1-decene, and 4- and/or 5-decene within the $C_{10}$ olefin composition are readily apparent to those skilled in the art with the aid of this disclosure.

In some aspects, the $C_{10}$ olefin composition is a $C_{10}$ olefin composition containing $C_{10}$ olefins as described herein that is substantially devoid of heteroatomic compounds. Examples of heteroatomic compounds include amines (e.g., pyrroles), peroxides, and alcohols (e.g., ethyl hexanol). "Substantially devoid of heteroatomic compounds" as used herein means a concentration of heteroatomic compounds which is less than 1, 0.1, 0.01, 0.001, or 0.0001 mass % based on a total mass of the $C_{10}$ olefin composition.

Methods for making/obtaining a $C_{10}$ olefin composition containing the above-described $C_{10}$ olefins are disclosed in U.S. Patent Application Publication No. 2018/0016204.

Any suitable metathesis catalyst system can be used in the metathesis step. Non-limiting examples of the metathesis catalyst system can include a metal oxide based metathesis catalyst system, a metal halide based metathesis catalyst system, a metal carbene based metathesis catalyst system, or any combination thereof. In one aspect, the metathesis catalyst system can be a metal oxide based metathesis catalyst system or a metal halide based metathesis catalyst system; alternatively, a metal oxide based metathesis catalyst system; alternatively, a metal halide based metathesis catalyst system; or alternatively, a metal carbene based metathesis catalyst system.

Metal oxide based metathesis catalyst systems can comprise (or consist essentially of, or consist of) cobalt oxide, molybdenum oxide, tungsten oxide, rhenium oxide, or any combination thereof. For instance, the metal oxide based catalyst system can comprise (or consist essentially of, or consist of) cobalt oxide; alternatively, molybdenum oxide; alternatively, tungsten oxide; or alternatively, rhenium oxide. Optionally, the metal oxide based metathesis catalyst system can further comprise a support, or a metal alkyl activator, or both a support and a metal alkyl activator. Illustrative supports can include alumina, silica, silica-alumina, and aluminum-phosphate, amongst other solid oxide materials. Accordingly, non-limiting examples of supported metal oxide based metathesis catalyst systems can include molybdenum oxide on alumina ($MoO_3/Al_2O_3$), tungsten oxide on silica ($WO_3/SiO_2$), rhenium oxide on alumina ($Re_2O_7/Al_2O_3$), cobalt oxide and molybdenum oxide on alumina ($CoO/MoO_3/Al_2O_3$), or rhenium oxide on alumina activated with tetramethyl tin ($Re_2O_7/Al_2O_3/SnMe_4$). Other suitable metal oxide based metathesis catalyst systems are known to those skilled in the art.

The metal oxide based metathesis catalyst system can further include a metal alkyl activator. In an aspect, the metal alkyl can comprise, can consist essentially of, or can be an alkyl lithium, an alkyl magnesium, an alkyl aluminum, alkyl tin compounds, or any mixture thereof. In an aspect, the metal alkyl activator can be an alkyl lithium compound. In another aspect, the metal alkyl activator can comprise, can consist essentially of, or can be an alkyl magnesium compound; alternately an alkyl aluminum compound; or alternatively, an alkyl tin compound. Non-limiting examples of alkyl aluminum compounds can include trialkyl aluminum compounds and/or alkyl aluminum halide compounds. The alkyl groups on the metal alkyl activator can include any $C_1$ to $C_{10}$ hydrocarbyl group, or alternatively, any $C_1$ to $C_5$ hydrocarbyl group. In various embodiments, the alkyl group for the metal alkyl activator can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group; alternatively, an n-butyl group; alternatively, a sec-butyl group; or alternatively, a tert-butyl group. Representative examples of suitable trialkyl aluminum compounds can include trimethylaluminum, triethylaluminum, triisobutylaluminum, or combinations thereof. The halide of the alkyl aluminum halide compound can be chloride, bromide, or iodide; alternatively, chloride; alternatively, bromide; or alternatively, iodide. Examples of suitable alkyl aluminum halide compounds can include ethylaluminum dichloride, diethylaluminum chloride, ethylaluminum sesquichloride, or combinations thereof. Suitable and non-limiting examples of alkyl tin compounds can include tetramethyl tin, tetraethyl tin, tetrabutyl tin, or combinations thereof.

Metal halide based metathesis catalyst systems can comprise (or consist essentially of, or consist of) a halide of tungsten, a halide of molybdenum, or a combination thereof. For instance, the metal halide based metathesis catalyst system can comprise (or consist essentially of, or consist of) a halide of tungsten; or alternatively, a halide of molybdenum. The halide of the metal halide based metathesis catalyst system can be chloride, bromide, or iodide. In an aspect, the halide can comprise, consist essentially of, or can be, chloride; alternatively, bromide; or alternatively, iodide. Hence, the metal halide based metathesis catalyst system can comprise (or consist essentially of, or consist of) tungsten chloride, molybdenum chloride, or a mixture thereof; alternatively, tungsten chloride; or alternatively, molybdenum chloride.

Optionally, the metal halide based metathesis catalyst system can further comprise a metal alkyl activator (as described herein), oxygen, an alcohol, or any combination thereof; alternatively, a metal alkyl activator; alternatively, oxygen; or alternatively, an alcohol. Non-limiting examples of metal halide based metathesis catalyst systems can include tungsten chloride/tetrabutyl tin ($WCl_6/SnMe_4$), tungsten chloride/ethylaluminum dichloride ($WCl_6/EtAlCl_2$), tungsten chloride/ethylaluminum dichloride/ethyl alcohol ($WCl_6/EtAlCl_2/EtOH$), molybdenum chloride/triethyl aluminum ($MoCl_5/AlEt_3$), or molybdenum chloride/triethyl aluminum/$O_2$ ($MoCl_5/AlEt_3/O_2$). Other suitable metal halide based metathesis catalyst systems are known to those skilled in the art.

The metal of the metal carbene based metathesis catalyst systems can comprise (or consist essentially of, or consist of) tungsten, tantalum, osmium, molybdenum, ruthenium, or any combination thereof. For instance, the metal of the metal carbene based metathesis catalyst system can comprise (or consist essentially of, or consist of) tungsten; alternatively, tantalum; alternatively, osmium; alternatively, molybdenum; or alternatively, ruthenium. These metal carbene based metathesis catalyst systems can contain compounds which have a stable metal-carbon double bond or can form a metal-carbon double bond in situ from a metal precursor having a stable metal-carbon single bond.

In an aspect, a ruthenium carbene based metathesis catalyst system can comprise a compound having the structure $L^1L^2X_2Ru=CHR^1$, wherein $L^1$ and $L^2$ can be an organic ligand, X can be a halide, and $R^1$ can be hydrogen or a hydrocarbyl group. Generally, the compound in the ruthenium carbene based metathesis catalyst system having the structure $L^1L^2X_2Ru=CHR^1$ can be described using any combination of $L^1$, $L^2$, X, or $R^1$ described herein.

Generally, $L^1$ and $L^2$ independently can be $R'_3P$, an imidazolinylidene group, or an imidazolidinylidene group. In some aspects, $L^1$ and $L^2$ can be $R'_3P$; alternatively, $L^1$ can be $R'_3P$ and $L^2$ can be an imidazolinylidene group or an imidazolidinylidene group; alternatively, $L^1$ can be $R'_3P$ and $L^2$ can be an imidazolinylidene group; alternatively, $L^1$ can be $R'_3P$ and $L^2$ can be an imidazolidinylidene group; alternatively, $L^1$ and $L^2$ can be imidazolinylidene groups; or alternatively, $L^1$ and $L^2$ can be imidazolidinylidene groups. In aspects, R' can be a hydrocarbyl group, where each R' of $R'_3P$ can be the same; alternatively, each R' of $R'_3P$ can be different; or alternatively, one R' of $R'_3P$ can be different from the other two R' groups. In some aspects, each R' of $R'_3P$ independently can be a $C_1$ to $C_{15}$ hydrocarbyl group; or alternatively, a $C_1$ to $C_{10}$ hydrocarbyl group. In other aspects, each hydrocarbyl R' of $R'_3P$ independently can be an alkyl group or an aromatic group; alternatively, an alkyl group; or alternatively, an aromatic group. In an aspect, each alkyl R' of $R'_3P$ independently can be a methyl group, ethyl group, n-propyl group, isopropyl group, tert-butyl group, neo-pentyl group, cyclopentyl group, or cyclohexyl group. In some aspects, one or more R' groups of $R'_3P$ can be a phenyl group, or alternatively, a substituted phenyl group. In an aspect, the substituents of any substituted phenyl group independently can be a $C_1$-$C_5$ organyl group, or alternatively, a $C_1$-$C_5$ hydrocarbyl group. In some aspects, $R'_3P$ can be a trialkyl phosphine or triphenyl phosphine; alternatively, a trialkyl phosphine; or alternatively, triphenyl phosphine. In an aspect, $R'_3P$ can be trimethyl phosphine, triethyl phosphine, triisopropyl phosphine, tri-tert-butyl phosphine, tri-neopentyl phosphine, tricyclopentyl phosphine, tricyclohexyl phosphine, or triphenyl phosphine; alternatively, triisopropyl phosphine, tri-tert-butyl phosphine, tri-neopentyl phosphine, tricyclopentyl phosphine, tricyclohexyl phosphine, or triphenyl phosphine; alternatively, tricyclopentyl phosphine, tricyclohexyl phosphine, or triphenyl phosphine; alternatively, tricyclopentyl phosphine or tricyclohexyl phosphine; alternatively, tricyclopentyl phosphine; alternatively, tricyclohexyl phosphine; or alternatively triphenyl phosphine.

In an aspect, the imidazolinylidene group or imidazolidinylidene group can be a $C_3$ to $C_{80}$ imidazolinylidene group or imidazolidinylidene group; alternatively, a $C_3$ to $C_{50}$ imidazolinylidene group or imidazolidinylidene group; or alternatively, a $C_5$ to $C_{40}$ imidazolinylidene group or imidazolidinylidene group. In some aspects, the imidazolinylidene group can be a 1,3-disubstituted imidazolinylidene group. In some aspects, the imidazolidinylidene group can be a 1,3-disubstituted imidazolidinylidene group. In an aspect, the 1,3-substituents of the 1,3-disubstituted imidazolinylidene group or 1,3-disubstituted imidazolidinylidene group independently can be any suitable hydrocarbyl group. In an aspect, the 1,3-substituents of the 1,3-disubstituted imidazolinylidene group or 1,3-disubstituted imidazolidinylidene group independently can be a $C_1$ to $C_{30}$ hydrocarbyl group. In some aspects, the 1,3-substituents of the 1,3-disubstituted imidazolinylidene group or 1,3-disubstituted imidazolidinylidene group independently can be a $C_6$ to $C_{20}$ aromatic group or a $C_1$ to $C_{10}$ alkyl group. In other aspects, the 1,3-substituents of the 1,3-disubstituted imidazolinylidene group or 1,3-disubstituted imidazolidinylidene group independently can be a $C_6$ to $C_{20}$ aromatic group, or alternatively, a $C_1$ to $C_{10}$ alkyl group. In an aspect, each aromatic group of the 1,3-disubstituted imidazolinylidene group or 1,3-disubstituted imidazolidinylidene group independently can be a substituted aromatic group. In some aspects, the substituted aromatic group of the 1,3-disubstituted imidazolinylidene group or 1,3-disubstituted imidazolidinylidene group can be a 2-disubstituted phenyl group, a 2,6-disubstituted phenyl group, or a 2,4,6-trisubstituted phenyl group; alternatively, a 2,6-disubstituted phenyl group; or alternatively, a 2,4,6-trisubstituted phenyl group. Suitable substituents for any substituted phenyl group within the 1,3-disubstituted imidazolinylidene group or 1,3-disubstituted imidazolidinylidene group can include any $C_1$ to $C_{10}$ hydrocarbyl group, or alternatively, any $C_1$ to $C_5$ hydrocarbyl group. In some aspects, each hydrocarbyl substituent independently can be a methyl group, ethyl group, n-propyl group, iso-propyl group, n-butyl group, sec-butyl group, or tert-butyl group; alternatively, a methyl group, ethyl group, n-butyl group, sec-butyl group, or tert-butyl group; alternatively, a methyl group; alternatively, an ethyl group, alternatively, an isopropyl group; or alternatively, a tert-butyl group. In some aspects, each substituted aromatic group of the 1,3-disubstituted imidazolinylidene group or 1,3-disubstituted imidazolidinylidene group independently can be a 2,6-diisopropylphenyl group or a 2,4,6-trimethylphenyl group; alternatively, a 2,6-diisopropylphenyl group; or alternatively, a 2,4,6-trimethyl-phenyl group.

In various aspects, each X of the compound having the structure $L^1L^2X_2Ru=CHR^1$ independently can be chloride, bromide, or iodide; alternatively, chloride; alternatively, bromide; or alternatively iodide. $R^1$ of the compound having the structure $L^1L^2X_2Ru=CHR^1$ can be hydrogen or a $C_1$ to $C_{20}$ hydrocarbyl group. In some aspects, $R^1$ can be a methyl group, an ethyl group, an isopropyl group, a tert-butyl group, a phenyl group, a 2-methyl-2-propene group, or a 2,2-diphenylethene group. In other aspects, $R^1$ can be a tert-butyl group, a phenyl group, a 2-methyl-2-propene group, or a 2,2-diphenylethene group; alternatively, hydrogen; alternatively, a tert-butyl group; alternatively, a phenyl group; alternatively, a tert-butyl group; alternatively, a phenyl group; alternatively, a 2-methyl-2-propene group; or alternatively, a 2,2-diphenylethene group.

In some non-limiting aspects, the ruthenium carbene based metathesis catalyst system can comprise, consist essentially of, or can be, dichloro(phenylmethylene) bis (tricyclohexyl phosphine) ruthenium, dichloro(3-methyl-2-butenylidene) bis(tricyclohexyl phosphine) ruthenium, dichloro(3-methyl-2-butenylidene) bis(tricyclopentyl phosphine) ruthenium, 1,3-bis-(2,4,6-trimethylphenyl)-2-(imidazolidinyl-idene)(phenylmethylene)dichloro(tricyclohexyl phosphine) ruthenium, or 1,3-bis-(2,6-diisopropylphenyl)-2-(imidazolidinylidene)(phenylmethylene)dichloro(tricyclohexyl phosphine) ruthenium. In some aspects, the ruthenium carbene based metathesis catalyst system can comprise, consist essentially of, or can be, dichloro-(phenylmethylene) bis(tricyclohexyl phosphine) ruthenium; alternatively, dichloro(3-methyl-2-butenylidene) bis(tricyclohexyl phosphine) ruthenium; alternatively, 1,3-bis-(2,4,6-trimethylphenyl)-2-(imidazolidinylidene)(phenylmethylene)dichloro(tricyclohexyl phosphine) ruthenium; or alternatively, 1,3-bis-(2,6-diisopropylphenyl)-2-(imidazolidinylidene)(phenylmethylene)dichloro(tricyclohexyl phosphine) ruthenium.

In an aspect, a molybdenum carbene based metathesis catalyst system can comprise a compound having the structure Mo(=CHR$^2$)(NAr)(OR$^3$)$_2$, wherein R$^2$ is a hydrogen or hydrocarbyl group, Ar is a substituted aromatic ring, and R$^3$ is a hydrocarbyl group or a halogenated hydrocarbyl group. Generally, the compound in the molybdenum carbene based metathesis catalyst system having the structure Mo(=CHR$^2$)(NAr)(OR$^3$)$_2$ can be described using any combination of R$^2$ described herein, Ar described herein, and R$^3$ described herein.

In some aspects, R$^2$ of the compound having the structure Mo(=CHR$^2$)(NAr)(OR$^3$)$_2$ can be hydrogen or a $C_1$ to $C_{20}$ hydrocarbyl group; or alternatively, a $C_1$ to $C_{20}$ hydrocarbyl group. In some aspects, R$^2$ can be a methyl group, an ethyl group, an isopropyl group, a tert-butyl group, a phenyl group, a 2-methyl-2-propene group, or a 2,2-diphenylethene group. In other aspects, R$^2$ can be a tert-butyl group, a phenyl group, a 2-methyl-2-propene group, or a 2,2-diphenylethene group; alternatively, a tert-butyl group or a phenyl group; alternatively, hydrogen; alternatively, a tert-butyl group; alternatively, a phenyl group; alternatively, a 2-methyl-2-propene group; or alternatively, a 2,2-diphenylethene group.

In an aspect, the substituted aromatic ring, Ar, of the compound having the structure Mo(=CHR$^2$)(NAr)(OR$^3$)$_2$ can be a $C_6$ to $C_{30}$ aromatic group, or alternatively, a $C_6$ to $C_{20}$ aromatic group. In some aspects, each substituent of the substituted aromatic ring, Ar, independently can be a $C_6$ to $C_{20}$ hydrocarbyl group, a $C_1$ to $C_{10}$ hydrocarbyl group, or a $C_1$ to $C_5$ hydrocarbyl group. In some aspects, the substituted aromatic ring, Ar, can be a 2-substituted phenyl group, a 2,6-disubstituted phenyl group, or a 2,4,6-trisubstituted phenyl group. In an aspect, each substituent of the substituted aromatic ring independently can be a methyl group, an ethyl group, an isopropyl group, a tert-butyl group, or a neopentyl group; alternatively, a methyl group, an isopropyl group, or a tert-butyl group; alternatively, a methyl group or an isopropyl group. In some aspects, each substituent of the substituted aromatic ring independently can be a methyl group; alternatively, an isopropyl group; or alternatively, a tert-butyl group. In some non-limiting aspects, the substituted aromatic ring, Ar, can be a 2-tert-butylphenyl group, a 2,6-dimethylphenyl group, a 2,6-diisopropylphenyl group, or a 2,4,6-trimethyl phenyl group; alternatively, a 2-tert-butylphenyl group; alternatively, a 2,6-dimethylphenyl group; alternatively, a 2,6-diisopropylphenyl group; or alternatively, a 2,4,6-trimethyl phenyl group.

In an aspect, each R$^3$ of the compound having the structure Mo(=CHR$^2$)(NAr)(OR$^3$)$_2$ independently can be a $C_1$ to $C_{10}$ organic group, or alternatively, a $C_1$ to $C_5$ organic group. In some aspects, the $C_1$ to $C_{10}$ or $C_1$ to $C_5$ organic group can be a hydrocarbylhalyl group (a group consisting of hydrogen, carbon, and halogen atoms); alternatively, a hydrocarbylfluoryl group (a group consisting of hydrogen, carbon, and fluorine atoms); or alternatively, a hydrocarbyl group. In an aspect, the halogen atoms of the hydrocarbylhalyl group can be fluorine, chlorine, bromine, iodine, or any combination thereof; alternatively, fluorine; alternatively, chlorine; alternatively, bromine; or alternatively, iodine. In some aspects, each R$^3$ independently can be a tert-butyl group or a hexafluoro-tert-butyl group. In other aspects, (OR$^3$)$_2$ can represent a single organic group wherein the two R$^3$ groups attached to the oxygen atoms are connected via a bond between any divalent, trivalent, or tetravalent atom within the R$^3$ groups. In further aspects, (OR$^3$)$_2$ can represent a single organic group wherein the two R$^3$ groups attached to the oxygen atoms are connected via a carbon-carbon bond between any carbon atom of the two R$^3$ groups.

In an aspect, the molybdenum carbene based metathesis catalyst system can comprise, consist essentially of, or can be, Mo(=CH—C(CH$_3$)$_3$)(N-2,6-diisopropylphenyl)(OC(CH$_3$)$_3$), Mo(=CH—C(CH$_3$)$_2$(C$_6$H$_5$))(N-2,6-diisopropylphenyl)(OC(CH$_3$)$_3$), Mo(=CH—C(CH$_3$)$_3$)(N-2,6-diisopropylphenyl)-(OC(CH$_3$)(CF$_3$)$_2$), or Mo(=CH—C(CH$_3$)$_2$(C$_6$H$_5$))(N-2,6-diisopropylphenyl)(OC(CH$_3$)(CF$_3$)$_2$). In other aspects, the molybdenum carbene based metathesis catalyst system can comprise, consist essentially of, or can be, Mo(=CH—C(CH$_3$)$_3$)N-2,6-diisopropylphenyl)(OC(CH$_3$)$_3$); alternatively, Mo(=CH—C(CH$_3$)$_2$(C$_6$H$_5$))-(N-2,6-diisopropylphenyl)(OC(CH$_3$)$_3$); alternatively, Mo(=CH—C(CH$_3$)$_3$)(N-2,6-diisopropylphenyl)-(OC(CH$_3$)(CF$_3$)$_2$); or alternatively, Mo(=CH—C(CH$_3$)$_2$(C$_6$H$_5$))(N-2,6-diisopropylphenyl)(OC(CH)(CF$_3$)$_2$).

Optionally, the metal carbene based metathesis catalyst system can further comprise a support. Illustrative supports can include alumina, silica, silica-alumina, and aluminum-phosphate, amongst other solid oxide materials. Additionally, the support can comprise a polymer, and the metal carbene metathesis catalyst compound can be tethered to the support via any of the ligands which do not contain the metal-carbon double bond.

A product, or a portion of the product, of the process(es) described herein is a composition comprising branched $C_{18}$ disubstituted internal olefins. In an embodiment, the composition comprising branched $C_{18}$ disubstituted internal olefins, can comprise at least 50, 60, 70, 75, 80, 85, 90, or 95 mole % branched $C_{18}$ disubstituted internal olefins. Description of the branched $C_{18}$ disubstituted internal olefins is divided into three groups; a first group of branched $C_{18}$ disubstituted internal olefins, a second group of branched $C_{18}$ disubstituted internal olefins, and a third group of branched $C_{18}$ disubstituted internal olefins. The description of the branched $C_{18}$ disubstituted internal olefins of the composition comprising branched $C_{18}$ disubstituted internal olefins can include one or more of branched $C_{18}$ disubstituted internal olefin(s) selected from the first group; alternatively, one or more of branched $C_{18}$ disubstituted internal olefin(s) selected from the first group and one or more of branched $C_{18}$ disubstituted internal olefin(s) selected from the second group; or alternatively, one or more of branched $C_{18}$ disubstituted internal olefin(s) selected from the first group, one or more of the branched $C_{18}$ disubstituted internal olefin(s) selected from the second group, and one or more of branched $C_{18}$ disubstituted internal olefin(s) selected from the third group.

In an aspect, the branched $C_{18}$ disubstituted internal olefins of the first group can include 5,12-dimethyl-8-hexadecene, 5-ethyl-11-methyl-7-pentadecene, 5-n-propyl-10-methyl-6-tetradecene, or any combination thereof. In one aspect, the branched $C_{18}$ disubstituted internal olefins can comprise only one, or only two, of 5,12-dimethyl-8-hexadecene, 5-ethyl-11-methyl-7-pentadecene, and 5-n-propyl-10-methyl-6-tetradecene. In another aspect, the branched $C_{18}$ disubstituted internal olefins can comprise 5,12-dimethyl-8-hexadecene, 5-ethyl-11-methyl-7-pentadecene, and 5-n-propyl-10-methyl-6-tetradecene.

In an aspect, the branched $C_{18}$ disubstituted internal olefins can include any amount of 5,12-dimethyl-8-hexadecene, 5-ethyl-11-methyl-7-pentadecene, and/or 5-n-propyl-10-methyl-6-tetradecene disclosed herein. In an aspect, 5,12-dimethyl-8-hexadecene, when present, can comprise at least 10, 11, 12, 13, 14, 15, 16, 17, or 18 mole % of the branched $C_{18}$ disubstituted internal olefins; alternatively or additionally, a maximum of (less than or equal to) 50, 45, 40, 38, 36, 34, or 32 mole % of the branched $C_{18}$ disubstituted internal olefins. In another aspect, the 5,12-dimethyl-8-hexadecene, when present, can comprise from any minimum mole % of the branched $C_{18}$ disubstituted internal olefins described herein to any maximum mole % of the branched $C_{18}$ disubstituted internal olefins described herein; for example from 10 mole % to 50 mole %, from 12 to 45 mole %, from 15 to 40 mole %, from 15 to 38 mole %, from 16 to 36 mole %, from 17 to 34 mole %, or from 18 to 32 mole % 5,12-dimethyl-8-hexadecene. In an aspect, 5-ethyl-11-methyl-7-pentadecene, when present, can comprise at least 10, 11, 12, 13, 14, 15, 16, or 17 mole % of the branched $C_{18}$ disubstituted internal olefins; alternatively or additionally, a maximum of (less than or equal to) 40, 35, 30, 27, 25, or 23 mole % of the branched $C_{18}$ disubstituted internal olefins. In another aspect, the 5-ethyl-11-methyl-7-pentadecene, when present, can comprise from any minimum mole % of the branched $C_{18}$ disubstituted internal olefins described herein to any maximum mole % of the branched $C_{18}$ disubstituted internal olefins described herein; for example from 10 mole % to 40 mole %, from 12 mole % to 35 mole %, from 14 mole % to 30 mole %, from 15 mole % to 27 mole %, from 16 mole % to 25 mole %, or from 17 mole 5 to 23 mole % 5-ethyl-11-methyl-7-pentadecene. In an aspect, 5-n-propyl-10-methyl-6-tetradecene, when present, can comprise at least 10, 11, 12, 13, 14, 15, 16, 17, 18, or 19 mole % of the branched $C_{18}$ disubstituted internal olefins; alternatively or additionally, a maximum of (less than or equal to) 45, 40, 35, 30, 28, or 26 mole % of the branched $C_{18}$ disubstituted internal olefins. In another aspect, the 5-n-propyl-10-methyl-6-tetradecene, when present, can comprise from any minimum mole % of the branched $C_{18}$ disubstituted internal olefins described herein to any maximum mole % of the branched $C_{18}$ disubstituted internal olefins described herein; for example from 10 mole % to 45 mole %, from 12 mole % to 40 mole %, from 14 mole % to 35 mole %, from 16 mole % to 30 mole %, from 18 mole % to 25 mole %, or from 19 mole % to 26 mole % 5-n-propyl-10-methyl-6-tetradecene. Generally, when the branched $C_{18}$ disubstituted internal olefins contain more than one of 5,12-dimethyl-8-hexadecene, 5-ethyl-11-methyl-7-pentadecene, and/or 5-n-propyl-10-methyl-6-tetradecene, the branched $C_{18}$ disubstituted internal olefins can comprise any individually disclosed mole % of 5,12-dimethyl-8-hexadecene disclosed herein, 5-ethyl-11-methyl-7-pentadecene herein, and/or 5-n-propyl-10-methyl-6-tetradecene disclosed herein.

In an aspect, the branched $C_{18}$ disubstituted internal olefins can additionally include branched $C_{18}$ disubstituted internal olefins from the second group of branched $C_{18}$ disubstituted internal olefins; i.e., 5,10-diethyl-7-tetradecene, 5-n-propyl-9-ethyl-6-tridecene, 5,8-di-n-propyl-6-dodecene, or any combination thereof. In one aspect, the branched $C_{18}$ disubstituted internal olefins can further comprise only one of, or only two of, 5,10-diethyl-7-tetradecene, 5-n-propyl-9-ethyl-6-tridecene, and 5,8-di-n-propyl-6-dodecene. In another aspect, the branched $C_{18}$ disubstituted internal olefins can further comprise 5,10-diethyl-7-tetradecene, 5-n-propyl-9-ethyl-6-tridecene, and 5,8-di-n-propyl-6-dodecene.

In an aspect, the branched $C_{18}$ disubstituted internal olefins can further comprise any amount of 5,10-diethyl-7-tetradecene disclosed herein, 5-n-propyl-9-ethyl-6-tridecene disclosed herein, and/or 5,8-di-n-propyl-6-dodecene disclosed herein. In an aspect, the 5,10-diethyl-7-tetradecene, when present, can comprise at least 0.5, 1, 1.5, or 2 mole % of the branched $C_{18}$ disubstituted internal olefins; alternatively or additionally, a maximum of (less than or equal to) 15, 12, 10, 8, or 6 mole % of the branched $C_{18}$ disubstituted internal olefins. In another aspect, 5,10-diethyl-7-tetradecene, when present, can comprise from any minimum mole % of the branched $C_{18}$ disubstituted internal olefins described herein to any maximum mole % of the branched $C_{18}$ disubstituted internal olefins described herein; for example from 0.5 mole % to 15 mole %, from 1 mole % to 12 mole %, from 1 mole % to 10 mole %, from 1.5 mole % to 8 mole %, or from 2 mole % to 6 mole % 5,10-diethyl-7-tetradecene. In an aspect, the 5-n-propyl-9-ethyl-6-tridecene, when present, can comprise at least 3, 4, 5, 6, or 7 mole % of the branched $C_{18}$ disubstituted internal olefins; alternatively or additionally, a maximum of (less than or equal to) 25, 22, 17, 15 or 13 mole % of the branched $C_{18}$ disubstituted internal olefins. In another aspect, 5-n-propyl-9-ethyl-6-tridecene, when present, can comprise from any minimum mole % of the branched $C_{18}$ disubstituted internal olefins described herein to any maximum mole % of the branched $C_{18}$ disubstituted internal olefins described herein; for example from 3 mole % to 25 mole %, from 4 mole % to 22 mole %, from 5 mole % to 17 mole %, from 6 mole % to 15 mole %, or from 7 mole % to 13 mole % 5-n-propyl-9-ethyl-6-tridecene. In an aspect, the 5,8-di-n-propyl-6-dodecene, when present, can comprise at least 2, 2.5, 3, 3.5, or 4 mole % branched $C_{18}$ disubstituted internal olefins; alternatively or additionally, a maximum of (less than or equal to) 20, 15, 12, 10, or 8 mole % of the branched $C_{18}$ disubstituted internal olefins. In another aspect, 5,8-di-n-propyl-6-dodecene, when present, can comprise from any minimum mole % of the branched $C_{18}$ disubstituted internal olefins described herein to any maximum mole % of the branched $C_{18}$ disubstituted internal olefins described herein; for example from 2 mole % to 20 mole %, from 2.5 mole % to 15 mole %, from 3 mole % to 12 mole %, from 3.5 mole % to 10 mole %, or from 4 mole % to 8 mole % 5,8-di-n-propyl-6-dodecene. Generally, when the branched $C_{18}$ disubstituted internal olefins further contain more than one of 5,10-diethyl-7-tetradecene, 5-n-propyl-9-ethyl-6-tridecene, and 5,8-di-n-propyl-6-dodecene, the branched $C_{18}$ disubstituted internal olefins can comprise any individually disclosed mole % of 5,10-diethyl-7-tetradecene disclosed herein, 5-n-propyl-9-ethyl-6-tridecene disclosed herein, and/or 5,8-di-n-propyl-6-dodecene disclosed herein.

In an aspect, the branched $C_{18}$ disubstituted internal olefins can additionally include branched Cis disubstituted internal olefins from a third group of branched $C_{18}$ disubstituted internal olefins, i.e., 5-methyl-8-heptadecene, 5-ethyl-7-hexadecene, 5-n-propyl-6-pentadecene, or any combination thereof. In one aspect, the branched $C_{18}$ disubstituted internal olefins can further comprise only one, or only two of, 5-methyl-8-heptadecene, 5-ethyl-7-hexadecene, and 5-n-propyl-6-pentadecene. In another aspect, the branched $C_{18}$ disubstituted internal olefins can further comprise 5-methyl-8-heptadecene, 5-ethyl-7-hexadecene, and 5-n-propyl-6-pentadecene.

In an aspect, the branched $C_{18}$ disubstituted internal olefins can further comprise any amount 5-methyl-8-heptadecene disclosed herein, 5-ethyl-7-hexadecene disclosed herein, and/or 5-n-propyl-6-pentadecene disclosed herein. In an aspect, the 5-methyl-8-heptadecene, when present, can comprise at least 2, 2.5, 3, 4, or 5 mole % branched $C_{18}$ disubstituted internal olefins; alternatively or additionally, a maximum of (less than or equal to) 20, 15, 12, 10, or 8 mole % of the branched $C_{18}$ disubstituted internal olefins. In another aspect, 5-methyl-8-heptadecene, when present, can comprise from any minimum mole % of the branched $C_{18}$ disubstituted internal olefins described herein to any maximum mole % of the branched $C_{18}$ disubstituted internal olefins described herein; for example from 2 mole % to 20 mole %, from 2.5 mole % to 15 mole %, from 3 mole % to 12 mole %, from 4 mole % to 10 mole %, or from 5 mole % to 8 mole % 5-methyl-8-heptadecene. In an aspect, the 5-ethyl-7-hexadecene, when present, can comprise at least 0.5, 1, 1.5, or 2 mole % of the branched $C_{18}$ disubstituted internal olefins; alternatively or additionally, a maximum of (less than or equal to) 15, 10, 8, 6, or 4 mole % of the branched $C_{18}$ disubstituted internal olefins. In another aspect, 5-ethyl-7-hexadecene, when present, can comprise from any minimum mole % of the branched $C_{18}$ disubstituted internal olefins described herein to any maximum mole % of the branched Cis disubstituted internal olefins described herein; for example from 0.5 mole % to 15 mole %, from 1 mole % to 10 mole %, from 1 mole % to 8 mole %, from 1.5 mole % to 6 mole %, or from 2 mole % to 4 mole % 5-ethyl-7-hexadecene. In an aspect, the 5-n-propyl-6-pentadecene, when present, can comprise at least 0.5, 1, 1.5, or 2 mole % of the branched $C_{18}$ disubstituted internal olefins; alternatively or additionally, a maximum of (less than or equal to) 15, 10, 8, 6, or 4 mole % of the branched $C_{18}$ disubstituted internal olefins. In another aspect, 5-n-propyl-6-pentadecene, when present, can comprise from any minimum mole % of the branched $C_{18}$ disubstituted internal olefins described herein to any maximum mole % of the branched $C_{18}$ disubstituted internal olefins described herein; for example from 0.5 mole % to 15 mole %, from 1 mole % to 10 mole %, from 1 mole % to 8 mole %, from 1.5 mole % to 6 mole %, or from 2 mole % to 4 mole % 5-n-propyl-6-pentadecene; or any combination thereof. Generally, when the branched $C_{18}$ disubstituted internal olefins further contain more than one of 5-methyl-8-heptadecene, 5-ethyl-7-hexadecene, and 5-n-propyl-6-pentadecene, the branched $C_{18}$ disubstituted internal olefins can comprise any individually disclosed mole % of 5-methyl-8-heptadecene disclosed herein, 5-ethyl-7-hexadecene disclosed herein, and/or 5-n-propyl-6-pentadecene disclosed herein.

In an aspect, the composition comprising branched $C_{18}$ disubstituted internal olefins, the metathesis product, and/or the liquid metathesis product, can additionally include 9-octadecene. In an aspect, 9-octadecene, when present, can comprise a maximum of (less than or equal to) 15, 10, 8, 6, 4, 2, or 1 mole % the composition comprising branched $C_{18}$ disubstituted internal olefins, or the liquid metathesis product.

In aspect, a process can comprise 1) contacting i) a $C_{10}$ olefin composition comprising branched $C_{10}$ olefins (or branched $C_{10}$ alpha olefins), and ii) a metathesis catalyst system; and 2) forming a liquid metathesis product comprising branched $C_{18}$ disubstituted internal olefins in a reaction zone (or metathesis reaction zone). In another aspect, a process can comprise 1) contacting i) a $C_{10}$ olefin composition comprising branched $C_{10}$ olefins (or branched $C_{10}$ alpha olefins), the branched $C_{10}$ olefins (or branched $C_{10}$ alpha olefins) comprising 3-propyl-1-heptene, 4-ethyl-1-octene, or methyl-1-nonene, and ii) a metathesis catalyst system; and 2) forming a liquid metathesis product comprising branched $C_{18}$ disubstituted internal olefins in a reaction zone (or metathesis reaction zone), where the branched $C_{18}$ disubstituted internal olefins can comprise 5,12-dimethyl-8-hexadecene, 5-ethyl-11-methyl-7-pentadecene, 5-n-propyl-10-methyl-6-tetradecene, or any combination thereof. In yet another aspect, a process can comprise 1) contacting i) a $C_{10}$ olefin composition comprising branched $C_{10}$ olefins (or branched $C_{10}$ alpha olefins), the branched $C_{10}$ olefins comprising 3-propyl-1-heptene, 4-ethyl-1-octene, and methyl-1-nonene, and ii) a metathesis catalyst system; and 2) forming a liquid metathesis product comprising branched $C_{18}$ disubstituted internal olefins in a reaction zone (or metathesis reaction zone), where the branched $C_{18}$ disubstituted internal olefins comprise 5,12-dimethyl-8-hexadecene, 5-ethyl-11-methyl-7-pentadecene, and 5-n-propyl-10-methyl-6-tetradecene. In an aspect the metathesis product can be formed under conditions capable of forming a metathesis product. In other aspects, the liquid metathesis product can further comprise branched $C_{18}$ disubstituted internal olefins from the second and/or third group of branched $C_{18}$ disubstituted internal olefins as described herein. The conditions capable of forming a metathesis product are described herein and can be utilized without limitation to further describe the processes described herein. It should be noted that when alpha olefins are utilized as a feedstock in the metathesis process, ethylene is also formed as a portion of the metathesis product. However, since ethylene is in gaseous form at normal temperature and pressure, ethylene is not considered as a part of the liquid metathesis product.

The reaction zone (or metathesis reaction zone) can comprise a reactor (or metathesis reactor) and optionally any equipment (e.g., pumps, compressors, valves, and piping) where the reaction conditions necessary to form metathesis product (or liquid metathesis product) are present. The process can operate as a batch process or as a continuous process and/or operate with or without recycle. Additionally, the process can utilize one or more reaction zones. Each reaction zone (or metathesis reaction zone) of the one or more reaction zones, independently can comprise one or more reactors (or metathesis reactors). In an aspect, each reactor of the one or more reaction zones can be a stirred tank reactor, a continuous-stirred tank reactor, a fixed bed reactor, or a plug flow reactor.

In aspects, the disclosed processes can include additional steps which can occur before contacting the branched $C_{10}$ olefins (or branched $C_{10}$ alpha olefins) and the metathesis catalyst system. Additional steps that can occur before contacting the branched $C_{10}$ olefins and the metathesis catalyst system can include separating (or removing) impurities from the $C_{10}$ olefin composition. For example, the $C_{10}$ olefin composition can contain heteroatomic compounds in addition to desirable branched $C_{10}$ olefins (or branched $C_{10}$ alpha olefins). The heteroatomic compounds, for example amines (e.g., pyrroles, among others), amides, peroxides, and alcohols (e.g., ethyl hexanol, among others), may be present in the $C_{10}$ olefin composition as isolated from the composition from which the $C_{10}$ olefin composition is obtained. Thus, in an aspect, the processes disclosed herein can include forming the $C_{10}$ olefin composition that is substantially devoid of heteroatomic compounds. For example, the process can comprise removing heteroatomic compounds from the $C_{10}$ olefin composition by distillation and/or contacting the $C_{10}$ olefin composition with an adsorbent; alternatively, distillation; or alternatively, contacting the $C_{10}$ olefin composition with an adsorbent. In an aspect, the adsorbent can comprise, can consist essentially of, or can be a silica, an alumina, a molecular sieve, a clay, a charcoal, a titania, a magnesia, a zirconia, an aluminosilicate, a zeolite, diatomaceous earth, or any combination thereof; alternatively, a silica, an alumina, a molecular sieve, a charcoal, an aluminosilicate, a zeolite, or any combination thereof; alternatively, a silica, an alumina, a molecular sieve, a charcoal; alternatively, a silica; alternatively, an alumina; alternatively, a molecular sieve; or alternatively, a charcoal.

Additional steps can occur after formation of the metathesis product, or liquid metathesis product. In an aspect, the processes described herein can further comprise discharging a reaction zone effluent (or a metathesis reaction zone effluent). In some aspects, the processes described herein can further comprise separating the metathesis catalyst system from the reaction zone effluent (or metathesis reaction zone effluent. As noted herein, the metathesis reaction can produce metathesis products that are in the liquid and gaseous phases at normal conditions. In aspects, recovering the liquid metathesis product can include recovering the liquid metathesis product. Additionally, the metathesis reaction can produce products which do not have the desired number of carbon atoms. Thus, in some aspects, the processes described herein can further comprise isolating a liquid metathesis product comprising branched $C_{18}$ disubstituted internal olefins, and/or isolating a composition comprising branched $C_{18}$ disubstituted internal olefins. In some aspects, gaseous metathesis product (e.g., ethylene) can also be recovered or removed from the reaction zone (or metathesis reaction zone) as a gaseous effluent separate from a liquid reaction zone effluent. In other aspects, a reaction zone effluent can be discharged from the reaction zone (or metathesis reaction zone) and a liquid metathesis product (and/or a composition comprising branched $C_{18}$ disubstituted internal olefins) recovered/isolated from the reaction zone effluent. In an aspect, the liquid metathesis product (and/or a composition comprising branched $C_{18}$ disubstituted internal olefins) can be separated/isolated using a separator such as a vapor/liquid separator and/or a distillation column.

In an aspect, the processes described herein can further comprise separating the liquid metathesis product from the reaction zone (or metathesis reaction zone) effluent and/or isolating the branched $C_{18}$ disubstituted internal olefins from the liquid metathesis product. In some aspects, the processes described herein can comprise separating the metathesis catalyst system from the reaction zone (or metathesis reaction zone) effluent (or liquid metathesis product). In an aspect, the reaction zone (or metathesis reaction zone) effluent (or liquid metathesis product) can be filtered or distilled to remove the metathesis catalyst system from the reaction zone (or metathesis reaction zone) effluent (or liquid metathesis product). In some aspects, the processes described herein can further comprise separating unconverted branched $C_{10}$ olefins from the reaction zone (or metathesis reaction zone effluent). In another aspect, the reaction zone (or metathesis reaction zone) effluent can be distilled in a distillation column (e.g., before or after metathesis catalyst system removal) to isolate the liquid metathesis product (or branched $C_{18}$ disubstituted internal olefins, or composition comprising or branched $C_{18}$ disubstituted internal olefins). In some aspects, the unconverted branched $C_{10}$ olefins can be recovered as an overhead product from the distillation column and the branched $C_{18}$ disubstituted internal olefins are recovered as a bottom product from the distillation column. In aspects where distillation is performed before the metathesis catalyst system has been removed, the bottom product from the distillation column can contain the metathesis catalyst system or components of the metathesis catalyst system. In an aspect, the metathesis catalyst system or components of the metathesis catalyst system can be removed from the bottom product by filtration. In aspects, where the metathesis catalyst system or components of the metathesis catalyst system are removed from the reaction zone (or metathesis reaction zone) effluent, or liquid metathesis product, by distillation and/or filtration, the reaction zone (or metathesis reaction zone) effluent, or liquid metathesis product can be substantially devoid of metathesis catalyst system or components of the metathesis catalyst system. In some aspects, the branched $C_{18}$ disubstituted internal olefins can be substantially devoid of metathesis catalyst system or components of the metathesis catalyst system. "Substantially devoid of metathesis catalyst system or components of the metathesis catalyst system" as used herein means a concentration of metathesis catalyst system or components of the metathesis catalyst system which is less than 1, 0.1, 0.01, 0.001, or 0.0001 mass % based on a total mass of the reaction zone (or metathesis reaction zone) effluent, liquid metathesis product, branched $C_{18}$ disubstituted internal olefins, or composition comprising branched $C_{18}$ disubstituted internal olefins.

In another aspect, the processes described herein can further comprise a feeding the ethylene recovered from the metathesis process to another petrochemical process. In some aspects, the processes described herein can be located in a plant site that also contains other processes for the treatment and/or production of petrochemicals, such as the oligomerization and/or polymerization of olefins, and in particular, ethylene. The ethylene which can be produced by the process described herein can be fed to one or more of these petrochemical processes for use therein. In an aspect, the ethylene can be fed to an oligomerization processor to a polymerization process.

Any conditions capable of forming a metathesis product can be utilized in the processes described herein, as would be recognized by those skilled in the art in view of this disclosure, for example process conditions as set forth in U.S. Patent Application Publication No. 2003/0135080 and U.S. Pat. No. 8,765,984. Metathesis conditions capable of forming a metathesis product can include, but are not limited to, pressure, temperature, time, and concentration (in relations to solution phase formation of the metathesis product) and are independently described herein. These independently described conditions can be utilized in any combination and without limitation, to further described the process disclosed herein.

Generally, the pressure which can be utilized to form the metathesis product (or the liquid metathesis product) can be any pressure capable of forming the metathesis product (or the liquid metathesis product). In an aspect, a minimum pressure which can be utilized to form the metathesis product (or the liquid metathesis product) can be 5 psia (34.5 kPa), 10 psia (68.9 kPa), 14 psia (96.5 kPa), 14.7 psia (101.4 kPa), 20 psia (138.9 kPa), or 50 psia (344.7 kPa); alternatively or additionally, a maximum pressure of 450 psia (3.1 MPa), 350 psia (2.4 MPa), 250 psia (1.7 MPa), or 150 psia (1.0 MPa). Ranges of pressure which can be utilized to form the metathesis product (or the liquid metathesis product) can range from any minimum pressure to any maximum pressure described herein for metathesis conditions. In some aspects, suitable ranges for the pressure which can be utilized to form the metathesis product (or the liquid metathesis product can include, but are not limited to, from 5 psia (34.5 kPa) to 450 psia (3.10 MPa); alternatively, from 10 psia (68.9 kPa) to 350 psia (2.4 MPa); alternatively, from 14 psia (96.5 kPa) to 250 psi (1.7 MPa); alternatively, from 14 psia (96.5 kPa) to 150 psia (1.0 MPa); alternatively, from 14.7 psia (101.4 kPa) to 150 psia (1.0 MPa); or alternatively, from 20 psia (138.9 kPa) to 150 psia (1.0 MPa). Other pressure ranges which can be utilized to form the metathesis product (or the liquid metathesis product) are readily apparent to those skilled in the art with the aid of this disclosure.

Generally, the metathesis product (or liquid metathesis product) can be formed at any temperature capable of forming a metathesis product (or a liquid metathesis product). In an aspect, the minimum temperature which can be utilized to form the metathesis product (or liquid metathesis product) can be 30° C., 35° C., 40° C., 45° C., or 50° C.; alternatively or additionally, the maximum temperature which can be utilized to form the metathesis product (or liquid metathesis product) can be 150° C., 140° C., 130° C., 120° C., 110° C., 90° C., 80° C., 70° C., or 60° C. Ranges for the temperature which can be utilized to form the metathesis product (or liquid metathesis product) can range from any minimum temperature described herein to any maximum temperature described herein. In some aspects, suitable ranges for the temperature which can be utilized to form the metathesis product (or liquid metathesis product) can include, but are not limited to, from 30° C. to 150° C.; alternatively, from 35° C. to 100° C.; alternatively, from 40° C. to 90° C.; alternatively, from 45° C. to 80° C.; alternatively, from 50° C. to 70° C.; alternatively, from 50° C. to 65° C.; or alternatively, from 50° C. to 60° C. Other temperature ranges which can be utilized to form the metathesis product (or the liquid metathesis product) are readily apparent to those skilled in the art with the aid of this disclosure.

Generally, the metathesis product (or liquid metathesis product) can be formed over any time period (or average time period) necessary to form the desired quantity of metathesis product; alternatively, provide a desired metathesis catalyst system productivity; alternatively, a desired conversion of a $C_{10}$ olefin composition (or branched $C_{10}$ olefins or branched $C_{10}$ alpha olefins) disclosed herein. In an aspect, the $C_{10}$ olefin composition (or branched $C_{10}$ olefins or branched $C_{10}$ alpha olefins) conversion can be at least 50 mass %, 60 mass %, 70 mass %, or 80 mass %). In an aspect, the minimum time (or minimum average time) which can be utilized to form the metathesis product (or liquid metathesis product) can be 1 second, 1 minute, 2 minutes, 4 minutes, 6 minutes, 8 minutes, or 10 minutes; alternatively or additionally, maximum time (or average maximum time) can be 1 hour, 1.5 hours, 2 hours, 4 hours, 6 hours, 8 hours, or 10 hours. Ranges for the time (or average time) which can be utilized to form the metathesis product (or liquid metathesis product) range from any minimum time to any maximum time described herein for metathesis conditions. In some aspects, suitable ranges for the time (or average time) which can be utilized to form the metathesis product (or liquid metathesis product) can include, but are not limited to, from 1 second to 10 hours; alternatively, from 1 minute to 8 hours; alternatively, from 2 minutes to 6 hours; alternatively, from 4 minutes to 4 hours; alternatively, from 6 minutes to 2 hours; alternatively, from 8 minutes to 90 minutes; or alternatively, from 10 minutes to 1 hour. Other time (or average time) ranges which can be utilized to form the metathesis product (or the liquid metathesis product) are readily apparent to those skilled in the art with the aid of this disclosure.

Generally, the metathesis product (or liquid metathesis product) can be formed using any concentration of the metathesis catalyst system which can produce the desired quantity of metathesis product, desired metathesis catalyst system productivity, and/or desired conversion of a $C_{10}$ olefin composition disclosed herein in the desired time (or average time). In an aspect, the minimum concentration for the metathesis catalyst system can be 100, 200, 300, 400, or 500 ppm by mass; alternatively or additionally, the maximum concentration for the metathesis catalyst system can be 1,000, 900, 800, 700, or 600 ppm by mass. Ranges the concentration of the catalyst system concentration which can be utilized can range from any minimum catalyst system concentration disclosed herein to any maximum time disclosed herein. In some aspects, suitable ranges for the concentration for the metathesis catalyst system which can be utilized to form the metathesis product (or the liquid metathesis product) can include, but are not limited to, 100 to 1,000 ppm, 110 to 900 ppm, 120 to 800 ppm, 130 to 700 ppm, or 130 ppm by mass. Other catalyst system concentration ranges which can be utilized to form the metathesis product (or the liquid metathesis product) are readily apparent to those skilled in the art with the aid of this disclosure. Generally, the ppm basis for the catalyst system concentration can be based upon the mass of the $C_{10}$ olefin composition (or branched $C_{10}$ olefins or branched $C_{10}$ alpha olefins).

In additional aspects, the metathesis product can be formed under an inert atmosphere, such as under a nitrogen blanket.

EXAMPLES

The following examples illustrate various aspects of the $C_{10}$ olefin composition and $C_{18}$ products obtained by metathesis reaction thereof.

Example 1

Example 1 demonstrates exemplary $C_{10}$ olefin compositions for use in metathesis reactions to produce the composition comprising branched $C_{18}$ olefins disclosed herein. Feedstock $C_{10}$ olefin compositions comprising branched $C_{10}$ olefins (or branched $C_{10}$ alpha olefins) were obtained by taking samples of a by-product $C_{10}$ olefin stream from a commercial plant employing selective ethylene trimerization to 1-hexene technology. Dimethyl pyrrole and other heteroatomic compounds contained in the sample were removed from the sample by contact with silica gel to produce the feedstock $C_{10}$ olefin compositions comprising branched $C_{10}$ olefins (or branched $C_{10}$ alpha olefins). The concentration of each component of the feedstock $C_{10}$ olefin compositions is reported as an average in the samples, a minimum in the samples, and a maximum in the samples is provided in Table 1.

TABLE 1

| Component | Average (mass %) | Minimum (mass %) | Maximum (mass %) |
|---|---|---|---|
| 1-decene | 4.8 | 3.6 | 6.0 |
| 2-butyl-1-hexene | 11.8 | 8.9 | 14.8 |
| 3-propyl-1-heptene | 17.4 | 13.1 | 21.8 |
| 4-ethyl-1-octene | 15.6 | 11.7 | 19.5 |
| 5-methyl-1-nonene | 38.2 | 28.7 | 47.8 |
| 4/5-decenes | 10.8 | 8.1 | 13.5 |

Example 2

The average values of the $C_{10}$ olefin compositions comprising branched $C_{10}$ olefins (or branched $C_{10}$ alpha olefins) identified in Table 1 were entered into a proprietary metathesis reaction simulator, developed by Chevron Phillips Chemical Company LP. The metathesis simulation produced the results for the liquid metathesis product is provided in Table 2.

TABLE 2

| Product | Mass % |
| --- | --- |
| 5,12-dimethyl-8-hexadecene | 25.5 |
| 5-ethyl-11-methyl-7-pentadecene | 20.7 |
| 5-n-propyl-10-methyl-6-tetradecene | 22.0 |
| 5,10-diethyl-7-tetradecene | 4.2 |
| 5-n-propyl-9-ethyl-6-tridecene | 9.2 |
| 5,8-di-n-propyl-6-dodecene | 5.8 |
| 5-methyl-8-heptadecene | 6.5 |
| 5-ethyl-7-hexadecene | 2.6 |
| 5-n-propyl-6-pentadecene | 3.0 |
| 9-octadecene | 0.5 |

As can be seen, 68.2 mass % of the product was attributable to three branched $C_{18}$ disubstituted internal olefins: 5,12-dimethyl-8-hexadecene, 5-ethyl-11-methyl-7-pentadecene, and 5-n-propyl-10-methyl-6-tetradecene, 9-octadecene is least favored, and the remaining branched $C_{18}$ disubstituted internal olefins of 5,10-diethyl-7-tetradecene, 5-n-propyl-9-ethyl-6-tridecene, 5,8-di-n-propyl-6-dodecene, 5-methyl-8-heptadecene, 5-ethyl-7-hexadecene, 5-n-propyl-6-pentadecene make up the balance of the liquid metathesis product.

Example 3

The metathesis reaction simulator was again used to determine potential concentration ranges for the liquid metathesis products based on the minimum and maximum values of the $C_{10}$ olefin compositions comprising branched $C_{10}$ olefins (or branched $C_{10}$ alpha olefins) identified in Table 1. The metathesis simulation produced the results for the liquid metathesis product provided in Table 3:

TABLE 3

| Product | Mass % |
| --- | --- |
| 5,12-dimethyl-8-hexadecene | 18-32 |
| 5-ethyl-11-methyl-7-pentadecene | 17-23 |
| 5-n-propyl-10-methyl-6-tetradecene | 19-26 |
| 5,10-diethyl-7-tetradecene | 2-6 |
| 5-n-propyl-9-ethyl-6-tridecene | 7-13 |
| 5,8-di-n-propyl-6-dodecene | 4-8 |
| 5-methyl-8-heptadecene | 6-7 |
| 5-ethyl-7-hexadecene | 2-4 |
| 5-n-propyl-6-pentadecene | 2-4 |
| 9-octadecene | 0-1 |

As can be seen, a large portion (54-81 mass %) of the product was attributable to three branched Cu, disubstituted internal olefins: 5,12-dimethyl-8-hexadecene, 5-ethyl-11-methyl-7-pentadecene, and 5-n-propyl-10-methyl-6-tetradecene, 9-octadecene is present in the smallest range of 0-1 mass %. The remaining branched $C_{18}$ disubstituted internal olefins of 5,10-diethyl-7-tetradecene, 5-n-propyl-9-ethyl-6-tridecene, 5,8-di-n-propyl-6-dodecene, 5-methyl-8-heptadecene, 5-ethyl-7-hexadecene, 5-n-propyl-6-pentadecene make up the majority of the balance (23-42 mass %) of the liquid metathesis product.

Example 4

A sample of a $C_{10}$ olefin composition having a $C_{10}$ distribution corresponding to the average distribution provided in Table 1 was treated with silica gel to remove polar species. The treated $C_{10}$ olefin composition, 500 grams, was combined with 130 ppm, by mass, of $2^{nd}$ Generation Grubbs Catalyst (1,3-bis(2,4,6-trimethylphenyl)-2-(imidazolidinylidene)(dichlorophenylmethylene)(tricyclohexylphosphine)-ruthenium) at 65° C. under nitrogen for two hours. During the reaction, gas bubbles of ethylene evolved and were vented away. After two hours, the reaction mixture was cooled and then washed with aqueous NaOH to remove catalyst residues. The organic and aqueous phases were separated. About 65 mass % of the organic mixture consisted of $C_{18}$ olefins, which were isolated by vacuum distillation. GC/FID analysis of the isolated organic product provided a chromatogram, illustrated in the FIGURE for the $C_{18}$ region the isolated organic product. The number and relative peak areas are consistent with the product mixture predicted from the metathesis simulation provided in Table 3. The GC/FID chromatogram of the $C_{18}$ region, illustrated in the FIGURE, showed three major peaks (peaks labeled 1, 2, and 3) having relative peak areas consistent with the predicted major metathesis product of Example 3: i.e., 5-n-propyl-10-methyl-6-tetradecene (peak 1), 5-ethyl-11-methyl-7-pentadecene (peak 2), and 5,12-dimethyl-8-hexadecene (peak 3). The GC/FID analysis also showed at least six 6 other $C_{18}$ isomers consistent with the predicted metathesis product of Example 3.

ADDITIONAL DISCLOSURE

The following is provided as additional disclosure for combinations of features and aspects of the present invention.

Statement 1. A composition comprising branched $C_{18}$ disubstituted internal olefins, wherein the branched $C_{18}$ disubstituted internal olefins comprise 5,12-dimethyl-8-hexadecene, 5-ethyl-11-methyl-7-pentadecene, 5-n-propyl-10-methyl-6-tetradecene, or any combination thereof.

Statement 2. A process comprising: 1) contacting i) a $C_{10}$ olefin composition comprising branched $C_{10}$ olefins, and ii) a metathesis catalyst system; and 2) forming a metathesis product comprising branched $C_{18}$ disubstituted internal olefins in a reaction zone, where the branched $C_{18}$ disubstituted internal olefins comprise 5,12-dimethyl-8-hexadecene, 5-ethyl-11-methyl-7-pentadecene, 5-n-propyl-10-methyl-6-tetradecene, or any combination thereof.

Statement 3. The process defined in statement 2, wherein the $C_{10}$ olefin composition comprising branched $C_{10}$ olefins comprises any minimum or range of branched $C_{10}$ olefins disclosed herein (e.g., at least 50 mole % branched $C_{10}$ olefins or from 50 mole % to 99.5 mole % branched $C_{10}$ olefins, among others disclosed herein).

Statement 4. The process defined in statement 2 or 3, wherein the branched $C_{10}$ olefins comprises 3-propyl-1-heptene, 4-ethyl-1-octene, and methyl-1-nonene.

Statement 5. The process defined in any one of statements 2-4, wherein the branched $C_{10}$ olefins comprise any minimum or range of 3-propyl-1-heptene, 4-ethyl-1-octene, and methyl-1-nonene disclosed herein (e.g., i) at least 8 mole % 3-propyl-1-heptene, ii) at least 6 mole % 4-ethyl-1-octene, and iii) at least 20 mole % 5-methyl-1-nonene, or i) from 8 mole % to 35 mole % 3-propyl-1-heptene, ii) from 6 mole % to 30 mole % 4-ethyl-1-octene, and iii) from 20 mole % to 65 mole % 5-methyl-1-nonene, among others disclosed herein).

Statement 6. The process defined in any one of statements 2-5, wherein the branched $C_{10}$ olefins further comprise 2-butyl-1-hexene.

Statement 7. The process defined in statement 6, wherein the branched $C_{10}$ olefins comprise any minimum or range of 2-butyl-1-hexene disclosed herein (e.g., at least 3 mole % 2-butyl-1-hexene or from 3 mole % to 25 mole % 2-butyl-1-hexene, among others disclosed herein).

Statement 8. The process defined in any one of statements 2-7, wherein the $C_{10}$ olefin composition comprises linear $C_{10}$ olefins.

Statement 9. The process defined in statement 8, wherein the linear $C_{10}$ olefins comprise any maximum or range of linear $C_{10}$ olefins disclosed herein (e.g., a maximum of 50 mole % linear $C_{10}$ olefins or from 0 mole % to 50 mole % linear $C_{10}$ olefins, among others disclosed herein).

Statement 10. The process defined in statement 8, wherein the linear $C_{10}$ olefins comprise i) 1-decene, ii) 4- and/or 5-decene, or iii) any combination of i) and ii).

Statement 11. The process defined in statement 10, wherein the linear $C_{10}$ olefins comprise any maximum or range of 1-decene disclosed herein (e.g., a maximum of 40 mole % 1-decene or from 0 mole % to 40 mole % 1-decene, among others disclosed herein).

Statement 12. The process defined in statement 10 or 11, wherein the linear $C_{10}$ olefins comprise any maximum or range of 4- and/or 5-decene disclosed herein (e.g., a maximum of 25 mole % linear $C_{10}$ olefins or from 0 mole % to 25 mole % linear $C_{10}$ olefins, among others disclosed herein).

Statement 13. The process defined in any one of statements 2-12, wherein the metathesis catalyst system is a metal oxide based metathesis catalyst system, a metal halide based metathesis catalyst system, a metal carbene based metathesis catalyst system, or any combination thereof.

Statement 14. The process defined in statement 13, wherein the metal oxide based metathesis catalyst system comprises cobalt oxide, molybdenum oxide, tungsten oxide, rhenium oxide, or any combination thereof.

Statement 15. The process defined in statement 14, wherein the metal oxide based metathesis catalyst system further comprises a support and/or a metal alkyl activator.

Statement 16. The process defined in statement 13, wherein the metal halide based metathesis catalyst system comprises a halide of tungsten, a halide of molybdenum, or any combination thereof.

Statement 17. The process defined in statement 16, wherein the metal halide based metathesis catalyst system further comprises a metal alkyl activator and/or oxygen or an alcohol.

Statement 18. The process of statement 13, wherein the metal carbene based metathesis catalyst system comprises tungsten, tantalum, osmium, molybdenum, ruthenium, or any combination thereof.

Statement 19. The process defined in statement 18, wherein the metal carbene based metathesis catalyst system further comprises a support.

Statement 20. The process defined in any one of statements 2-19, where the $C_{10}$ olefin composition is substantially devoid of heteroatomic compounds.

Statement 21. The process defined in statement 20, wherein the process further comprises the step of forming the $C_{10}$ olefin composition substantially devoid of heteroatomic compounds by removing heteroatomic compound from the $C_{10}$ olefin composition.

Statement 22. The process defined in statement 21, wherein the $C_{10}$ olefin composition is treated with an adsorbent to form the $C_{10}$ olefin composition substantially devoid of heteroatomic compounds.

Statement 23. The process defined in any one of statements 2-22, wherein the process further comprises: separating a stream comprising ethylene from the metathesis reactor system and recovering the liquid metathesis product.

Statement 24. The composition defined in statement 1 or the process defined in any one of statements 2-23, wherein the branched $C_{18}$ disubstituted internal olefins comprise 5,12-dimethyl-8-hexadecene, 5-ethyl-11-methyl-7-pentadecene, and 5-n-propyl-10-methyl-6-tetradecene.

Statement 25. The composition or process defined in statement 24, wherein the branched $C_{18}$ disubstituted internal olefins comprise any minimum or range of 5,12-dimethyl-8-hexadecene, 5-ethyl-11-methyl-7-pentadecene, and 5-n-propyl-10-methyl-6-tetradecene disclosed herein (e.g., at least 10 mole % 5,12-dimethyl-8-hexadecene, at least 10 mole % 5-ethyl-11-methyl-7-pentadecene, and at least 10 mole % 5-n-propyl-10-methyl-6-tetradecene; or from 18 mole % to 32 mole % 5,12-dimethyl-8-hexadecene, from 17 mole % to 23 mole % 5-ethyl-11-methyl-7-pentadecene, and from 19 mole % to 26 mole % 5-n-propyl-10-methyl-6-tetradecene; among others disclosed herein).

Statement 26. The composition defined in any one of statements 1 or 24-25, or the process defined in any one of statements 2-25, wherein the branched $C_{18}$ disubstituted internal olefins further comprise 5,10-diethyl-7-tetradecene, 5-n-propyl-9-ethyl-6-tridecene, 5,8-di-n-propyl-6-dodecene, or any combination thereof.

Statement 27. The composition or process defined in statement 26, wherein the branched $C_{18}$ disubstituted internal olefins further comprise 5,10-diethyl-7-tetradecene, 5-n-propyl-9-ethyl-6-tridecene, and 5,8-di-n-propyl-6-dodecene.

Statement 28. The composition or process defined in statement 26 or 27, wherein the branched $C_{18}$ disubstituted internal olefins comprise any minimum or range 5,10-diethyl-7-tetradecene, 5-n-propyl-9-ethyl-6-tridecene, and 5,8-di-n-propyl-6-dodecene disclosed herein (e.g., at least 1 mole % 5,10-diethyl-7-tetradecene, at least 3 mole % 5-n-propyl-9-ethyl-6-tridecene, and at least 3 mole % 5,8-di-n-propyl-6-dodecene; or from 2 mole % to 6 mole % 5,10-diethyl-7-tetradecene, from 7 mole % to 13 mole % 5-n-propyl-9-ethyl-6-tridecene, and from 4 mole % to 8 mole % 5,8-di-n-propyl-6-dodecene; among others disclosed herein).

Statement 29. The composition of one of statements 1 or 24-28, or the process of any one of statements 2-28, wherein the branched $C_{18}$ disubstituted internal olefins further comprise 5-methyl-8-heptadecene, 5-ethyl-7-hexadecene, 5-n-propyl-6-pentadecene, or any combination thereof.

Statement 30. The composition or the process defined in statement 29, wherein the branched $C_{18}$ disubstituted internal olefins further comprise 5-methyl-8-heptadecene, 5-ethyl-7-hexadecene, and 5-n-propyl-6-pentadecene.

Statement 31. The composition defined in any one of statements 1 or 24-30, or the process defined in any one of statements 2-30, wherein the metathesis product further comprises 9-octadecene.

Statement 32. The composition defined in any one of statements 1 or 24-31, or the process defined in any one of statements 2-31, wherein the composition is an additive for a lube oil.

Statement 33. The process defined in any one of statements 2-32, further comprising adding the composition to a lube oil.

Statement 34. A lube oil comprising the composition defined in any one of statements 1 or 24-32.

Statement 35. A feedstock for making a paper sizing agent comprising the composition defined in any one of statements 1 or 24-32.

Statement 36. The process defined in any one of statements 2-31, further comprising reacting the composition with maleic anhydride to form an alkenyl succinic anhydride.

While aspects of the disclosure have been shown and described, modifications thereof can be made without departing from the spirit and teachings of the invention. The aspects and examples described herein are exemplary only, and are not intended to be limiting. Many variations and modifications of the invention disclosed herein are possible and are within the scope of the invention.

At least one aspect is disclosed and variations, combinations, and/or modifications of the embodiment(s) and/or features of the embodiment(s) made by a person having ordinary skill in the art are within the scope of the disclosure. Alternative aspects that result from combining, integrating, and/or omitting features of the aspect(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, 5, 6, . . . ; greater than 0.10 includes 0.11, 0.12, 0.13, 0.14, 0.15 . . . ). For example, whenever a numerical range with a lower limit, $R_1$, and an upper limit, $R_u$, is disclosed, any number falling within the range is specifically disclosed. In particular, the following numbers within the range are specifically disclosed: $R=R_1+k*(R_u-R_1)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of.

Accordingly, the scope of protection is not limited by the description set out above but is only limited by the claims which follow, that scope including all equivalents of the subject matter of the claims. Each and every claim is incorporated into the specification as an aspect of the present invention. Thus, the claims are a further description and are an addition to the detailed description of the present invention. The disclosures of all patents, patent applications, and publications cited herein are hereby incorporated by reference.

What is claimed is:

1. A composition comprising branched $C_{18}$ disubstituted internal olefins, wherein the branched $C_{18}$ disubstituted internal olefins comprise 5,12-dimethyl-8-hexadecene, 5-ethyl-11-methyl-7-pentadecene, 5-n-propyl-10-methyl-6-tetradecene, or any combination thereof.

2. The composition of claim 1, wherein the branched $C_{18}$ disubstituted internal olefins comprise 5,12-dimethyl-8-hexadecene, 5-ethyl-11-methyl-7-pentadecene, and 5-n-propyl-10-methyl-6-tetradecene.

3. The composition of claim 2, wherein the branched $C_{18}$ disubstituted internal olefins further comprise 5,10-diethyl-7-tetradecene, 5-n-propyl-9-ethyl-6-tridecene, and 5,8-di-n-propyl-6-dodecene.

4. The composition of claim 3, wherein the branched $C_{18}$ disubstituted internal olefins further comprise 5-methyl-8-heptadecene, 5-ethyl-7-hexadecene, and 5-n-propyl-6-pentadecene.

5. The composition of claim 2, wherein the branched $C_{18}$ disubstituted internal olefins comprise at least 10 mole % 5,12-dimethyl-8-hexadecene, at least 10 mole % 5-ethyl-11-methyl-7-pentadecene, and at least 10 mole % 5-n-propyl-10-methyl-6-tetradecene.

6. The composition of claim 5, wherein the branched $C_{18}$ disubstituted internal olefins further comprise at least 1 mole % 5,10-diethyl-7-tetradecene, at least 3 mole % 5-n-propyl-9-ethyl-6-tridecene, and at least 3 mole % 5,8-di-n-propyl-6-dodecene.

7. The composition of claim 2, wherein the branched $C_{18}$ disubstituted internal olefins comprises from 18 mole % to 32 mole % 5,12-dimethyl-8-hexadecene, from 17 mole % to 23 mole % 5-ethyl-11-methyl-7-pentadecene, and from 19 mole % to 26 mole % 5-n-propyl-10-methyl-6-tetradecene.

8. The composition of claim 7, wherein the branched $C_{18}$ disubstituted internal olefins further comprise from 2 mole % to 6 mole % 5,10-diethyl-7-tetradecene, from 7 mole % to 13 mole % 5-n-propyl-9-ethyl-6-tridecene, and from 4 mole % to 8 mole % 5,8-di-n-propyl-6-dodecene.

9. The composition of claim 8, further comprising 9-octadecene.

10. A process comprising: 1) contacting i) a $C_{10}$ olefin composition comprising branched $C_{10}$ olefins, the branched $C_{10}$ olefins comprising 3-propyl-1-heptene, 4-ethyl-1-octene, and methyl-1-nonene, and ii) a metathesis catalyst system; and 2) forming a liquid metathesis product comprising branched $C_{18}$ disubstituted internal olefins in a reaction zone, where the branched $C_{18}$ disubstituted internal olefins comprise 5,12-dimethyl-8-hexadecene, 5-ethyl-11-methyl-7-pentadecene, 5-n-propyl-10-methyl-6-tetradecene, or any combination thereof.

11. The process of claim 10, wherein the branched $C_{10}$ olefins comprise at least 8 mole % 3-propyl-1-heptene, at least 6 mole % 4-ethyl-1-octene, and from 20 mole % to 65 mole % 5-methyl-1-nonene.

12. The process of claim 10, wherein the branched $C_{10}$ olefins comprise from 8 mole % to 35 mole % 3-propyl-1-heptene, from 6 mole % to 30 mole % 4-ethyl-1-octene, and from 20 mole % to 65 mole % 5-methyl-1-nonene.

13. The process of claim 10, wherein the branched $C_{18}$ disubstituted internal olefins comprise 5,12-dimethyl-8-hexadecene, 5-ethyl-11-methyl-7-pentadecene, and 5-n-propyl-10-methyl-6-tetradecene.

14. The process of claim 10, wherein the branched $C_{18}$ disubstituted internal olefins further comprises 5,10-diethyl-7-tetradecene, 5-n-propyl-9-ethyl-6-tridecene, and 5,8-di-n-propyl-6-dodecene.

15. The process of claim 10, wherein the $C_{10}$ olefin composition further comprises 1-decene.

16. The process of claim 15, wherein the branched $C_{18}$ disubstituted internal olefins further comprise 5-methyl-8-heptadecene, 5-ethyl-7-hexadecene, and 5-n-propyl-6-pentadecene.

17. The process of claim 16, wherein the liquid metathesis product further comprises 9-octadecene.

18. The process of claim 10, wherein the metathesis catalyst system comprises a metal oxide based metathesis catalyst system, a metal halide based metathesis catalyst system, a metal carbene based metathesis catalyst system, or any combination thereof.

19. The process of claim 18, wherein the metathesis catalyst system is the metal oxide based metathesis catalyst system, where the metal oxide based metathesis catalyst system comprises cobalt oxide, molybdenum oxide, tungsten oxide, rhenium oxide, or any combination thereof.

20. The process of claim 18, wherein the metathesis catalyst system is the metal halide based catalyst system where the metal halide based metathesis catalyst system comprises a halide of tungsten, a halide of molybdenum, or any combination thereof.

21. The process of claim 18, wherein the metathesis catalyst system is the metal carbene based metathesis catalyst system where the metal carbene based metathesis catalyst system comprises tungsten, tantalum, osmium, molybdenum, ruthenium, or any combination thereof.

22. The process of claim 10, wherein the $C_{10}$ olefin composition is a $C_{10}$ olefin composition substantially devoid of heteroatomic compounds.

23. The process of claim 22, further comprising forming the $C_{10}$ olefin composition substantially devoid of heteroatomic compounds by removing heteroatomic compounds from the $C_{10}$ olefin composition.

24. The process of claim 10, further comprising:

removing a stream comprising ethylene from the reaction zone; and recovering the liquid metathesis product from the reaction zone.

* * * * *